United States Patent [19]
Roncucci et al.

[11] Patent Number: 5,869,051
[45] Date of Patent: Feb. 9, 1999

[54] CONJUGATED TERTHIOPHENE AND FURAN COMPOUNDS WITH PHOTOENHANCED BIOCIDAL PROPERTIES

[75] Inventors: Gabrio Roncucci, Colle Val D'Elsa; Giovanni Neri, Via Rome, Siena, both of Italy

[73] Assignees: Giovanni Neri, Siena; L. Molenti & C. Dei Fratelli Alitti Societa' Di Esercizio Societa' Per Azioni, Scandicci, both of Italy

[21] Appl. No.: 750,021
[22] PCT Filed: May 22, 1995
[86] PCT No.: PCT/EP95/01938
  § 371 Date: Nov. 22, 1996
  § 102(e) Date: Nov. 22, 1996
[87] PCT Pub. No.: WO95/32001
  PCT Pub. Date: Nov. 30, 1995

[30] Foreign Application Priority Data

May 23, 1994 [IT] Italy .................. FI94A0095

[51] Int. Cl.⁶ .............. A61K 39/395; A61K 39/40; C07K 16/00; C07H 11/00
[52] U.S. Cl. .............. 424/181.1; 424/179.1; 424/1.53; 530/391.7; 536/115; 536/118; 540/1; 435/7.21
[58] Field of Search .............. 424/183.1, 236.1, 424/178.1, 181.1, 179.1, 1.53; 530/391.7, 1; 536/115, 118; 435/7.21

[56] References Cited

FOREIGN PATENT DOCUMENTS

| | | |
|---|---|---|
| 1173743 | 9/1984 | Canada . |
| 0454204 | 10/1991 | European Pat. Off. . |
| 0641796 | 3/1995 | European Pat. Off. . |

OTHER PUBLICATIONS

J. Invest. Dermatol., vol. 87, No. 3, 354–357, Aug. 1986.
Spikes et al., Chemical Abstract, vol. 118, No. 25, Jun. 21, 1993.
Mares et al., Chemical Abstract, vol. 123, No. 1, Jul. 3, 1995.
Klyashchitsky et al., J. Controlled Release, vol.29, 1–16, 1994.
Hudson et al., Chemical Abstract, vol. 119, No. 23, Dec. 6, 1993.
Hudson, J.B., et al, "Photoactive Antiviral and Cytotoxic Activities of Synthetic Thiophenes and Their Acetylenic Derivatives," *Chemosphere*, vol. 19 (1989), No. 8/9, pp. 1329–1343.
Hudson, J.B., et al, "Therapeutic Potential of Plant Photosensitizers," *Pharmac. Ther.*, vol. 49 (1991), pp. 181–222.
Hudson, J.B., et al, "Ultraviolet–Mediated Antibiotic Activity of Synthetic Thiophenes and Their Acetylenic Derivatives," vol. 18 (1989), Nos. 11/12, pp. 2317–2327.
Lavoie, Thomas B., et al., "Experimental Analysis by Site–Directed Mutagenesis of Somatic Mutation Effects on Affinity and Fine Specificity in Antibodies Specific for Lysonzyme," vol. 148, No. 2, Jan. 15, 1992, pp. 503–513.
Natali, P.G., et al, "Phenotyping of Lesions of Melanocyte Origin With Monoclonal Antibodies to Melanoma–Associated Antigens and to HLA Antigens," *JNCI*, vol. 73, No. 1, Hul. 1984, pp. 13–18.
Neri, Dario et al, "High–affinity Antigen Binding by Chelating Recombinant Antibodies (CRAbs)," *J. Mol. Biol.*, No. 246, (1995), pp. 365–373.
Winter, Greg, et al, "Man–made Antibodies," *Nature*, vol. 349, Jan. 24, 1991, pp. 293–299.
Berzofsky et al. Fundamental Immunology (W.E. Paul, ed.) Raven Press; Ch. 8, 1993.
Boch et al. Photochem. Photobiol. 59:875, May 1994.
Boch et al. Photochem. Photobiol. 64(1):92–99, 1996.
Ghose et al. Meth. Enzymol. 93:280–333, 1983.
Hudson et al. Photochem. Photobiol. 44(4):477–82, 1986.
Hudson et al. Chemosphere 19(8/9):1329–43, 1989.
MacEachern et al. Tetrahedron 44(9):2403–12, 1988.
Marles et al. Photochem. Photobiol 55(4):479–87, 1992.
Rossi et al. Tetrahedron 47(39):8443–60, 1991.

*Primary Examiner*—Lila Feisee
*Assistant Examiner*—Lin Sun-Hoffman
*Attorney, Agent, or Firm*—McDermott, Will & Emery

[57] ABSTRACT

Conjugates of a carrier molecule and an organic molecule producing singlet oxygen after irradiation are useful in diagnostic and therapeutic applications. The organic molecule is a terthienyl or terfuranyl compound derivatized to react with amino, thiol, or saccharide groups of the carrier molecule. Suitable carrier molecules include antibodies, peptides, haptamers, sugars, and other analogous molecules which direct the organic molecule to a biological target.

16 Claims, No Drawings

CONJUGATED TERTHIOPHENE AND FURAN COMPOUNDS WITH PHOTOENHANCED BIOCIDAL PROPERTIES

FIELD OF THE INVENTION

The present invention concernes conjugates consisting of a carrier molecule linked to an organic molecule able to efficiently produce singlet oxygen after irradiation suitably derivatized as to react with an amino or thiol group of the carrier molecule. Said conjugates are able to work out a biocidal action on various kinds of cells, either in vivo or in vitro, once activated with radiations in the near UV; they may be used either for therapeutical or diagnostic aim.

PRIOR ART

It is known that organic molecules, able to efficiently produce singlet oxygen as a result of irradiation, have photoenhanced biocidal activity. The biocidal activity of the molecules shows itself against essentially every living form such as viruses, fungi, bacteria, invertebrates, vertebrates, eukaryote cells [see J. B. Hudson et al.: Pharm. Ther. 49, 181 (1991); J. B. Hudson et al.: Chemosphere 19, 1329 (1989); J. B. Hudson et al.: Chemosphere 18, 2317 (1989)].

The biocidal properties make these molecules extremely interesting for a great number of applications in therapy. However the practical application of the above mentioned molecules is strongly limited because they are powerful contact allergens and cause, once administered and irradiated, erythemas, pruritus and hyperpigmentation for periods of weeks and months [see G. H. N. Towers et al.: Contact Dermatitis 5, 140 (1978); W. Rampone et al.: J. Invest. Dermatol. 87, 354 (1986)]. It is thus obvious the interest to develop compounds which, while keeping the desired biocidal capabilities, do not show the undesirable side effects.

DETAILED DESCRIPTION OF THE INVENTION

Now it has been surprisingly discovered that it is possible to remove the negative effects related to the use of the above mentioned molecules keeping unaltered their biocidal properties by conjugating the organic molecule able to produce efficiently singlet oxygen after irradiation to a carrier molecule able to direct it on a definite biological target.

According to a particular embodiment of the present invention the organic molecule able to produce efficiently singlet oxygen after irradiation is a molecule having general formula (I)

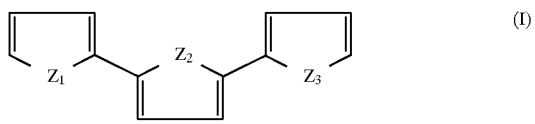

(I)

wherein $Z_1$, $Z_2$, $Z_3$ equal or different one another are S or O, suitably derivatized as to react with an amino or thiol group of the carrier molecule.

According to a further particular embodiment of the invention the organic molecule able to produce efficiently singlet oxygen as a result of irradiation is the 2,2':5',2"-terthiophene (hereinafter abbreviated as α-T) molecule having formula (I) in which $Z_1=Z_2=Z_3=S$.

According to the invention the carrier molecule is selected from the group consisting of: antibodies (native, monoclonal or recombinant) peptides, haptamers (nucleic acids with the capability of a selective bond toward a target), sugars, or other analogous carriers able to direct the derivative having formula (I) toward a biological target as for example the avidin-biotin conjugate.

In particular the terthienyl compound may be derivatized with a group able to react with amino groups (for example side chains of lysine residues in peptides or proteins), with thiol groups (for example side chains of cysteine), with suitably modified saccharide residues of the carrier molecule or with avidin and/or biotin utilizing the functional groups present in these molecules; these solutions allow to conjugate the terthienyl derivative with a wide spectrum of different molecules.

The derivatization of the terthienyl compound is carried out preferably in position 2.

When the terthienyl derivative is linked to Avidin and/or Biotin the conjugate object of the present invention may be directly formed in vivo separately administering the part formed by Biotin bound to the carrier molecule and the part formed by Avidin bound to the α-T derivative or vice versa.

The utility of these systems consists in the fact that they allow the administration of an inferior quantity of the α-T derivative without lowering the potential therapeutic efficiency of the molecule, making it available various α-T derivatives conjugated both to Biotin and Avidin. In this case the α-T system is mediated by the Avidin-Biotin bond ($K_{aff}=10^{15}$) which makes it possible the immobilization of the α-T molecule on the pathogenic agent in subsequent steps by binding the Avidin to the antibody and thereafter administrating the α-T molecule linked to Biotin or by using a biotinylated antibody, then giving Avidin and finally α-T linked to Biotin according to a three step protocol, or allows an amplification of the administrable α-T quantity (thanks to the tetravalency of the Avidin molecule).

The conjugate according to the invention, as previously defined, may be used either for the topical treatment of superficial diseases (melanomas, eye diseases, fungineous or viral skin infections) or vehiculated by intramuscular or intravenous way.

In the case of topical administration the compositions commonly provided for this aim will be used such as: ointments, creams, unguents containing the compound having formula (I) in combination with the suitable diluents known in the state of the art for this kind of applications.

The composition will be directly applied in the area of interest, then the part will be washed in order to reduce the presence of α-T near healthy cells but without compromising its localization on the pathogen and finally submitting the part to irradiation with light of the near ultraviolet (about 360 nm) or simply exposing the treated part to the sunlight.

In the case of the injections the active product will be dissolved in the suitable liquids physiologically acceptable for the preparation of injectable solutions.

In this case the subsequent irradiation, required to activate the molecule, may be carried out using optical fibres and the correlated surgical techniques.

Some examples of preparation of products according to the invention are described hereinafter for explicative but not limitative aim.

In particular, in the examples 1–7 afterwards reported the preparation of derivatives of the 2,2':5',2"terthienyl suitably functionalized in order to covalently react with amino groups present on the carrier molecule is described; in the examples 9–11 the functionalization is carried out to allow the analogous reaction with thiol groups present on the carrier molecule; in the example 12 the functionalization is carried out to allow the analogous reaction with saccharide groups.

In the example 13 the functionalization is carried out to allow the same reaction on thyrosine or hystidine residues.

Examples 14 and 15 refer to Biotin derivatives preparation. Examples 16–19 refer to conjugates preparation according to the invention; and finally the examples 20–26 describe tests on the biocidal activity of the considered products.

α-T DERIVATIVES REACTIVE TO AMINO GROUPS AND CORRESPONDING INTERMEDIATES

EXAMPLE 1

5-Formyl-2,2':5',2"-terthiophene [(α-T)-CHO]

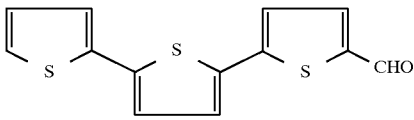

The preparation has been done according to the procedure described by R. Rossi et al. Tetrahedron 47, (39) 8443–60 (1991).

44.8 mmol of N-methylformanilide and 40.7 mmol of POCl$_3$ are mixed at room temperature and the solution stirred for 15'.

A solution of 2,2':5',2" terthiophene (40.7 mmol) is added in 200 ml of dichloromethane and the resulting mixture is stirred while refluxing for 40 h.

Then the mixture is poured in a 10% HCl solution, stirred for 1 h and extracted with dichloromethane.

The organic extracts, washed with a NaCl solution and dehydrated are then dry evaporated. The residue is purified by column chromatography (silica gel, benzene) to give a gold-yellow crystalline solid, m.p.: 137°–138° C.

EXAMPLE 2

Methyl(E)-3-(2,2':5',2"-terthien-5-yl)propenoate

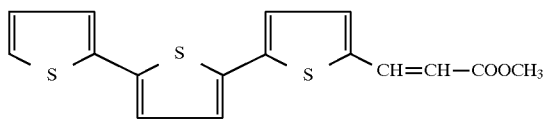

59 mg of sodium hydride are added to a solution of 358 mg of dimethylphosphono acetate in 50 ml of anhydrous THF, cooled to 0° C., and the resulting solution previously stirred for 30 minutes, is brought back to the room temperature by stirring for further 15 minutes.

500 mg (1.79 mmol) of the aldehyde obtained in the example 1 are then added portionwise, and the reaction mixture is stirred for two hours. Then the solvent is evaporated and the residue treated with water.

The yellow solid obtained is dried and crystallized from AcOEt; m.p.: 197°–199° C.

Analysis Calculated: C: 57.80 H: 3.64 Found: C: 57.27 H: 3.47

NMR (CDCl$_3$, 200 MHz): 7.24–7.01 (m, 7H, α-T); 7.73 (d, 1H, =CH—COOCH$_3$); 6.18 (d, 1H, α-T-CH=); 3.80 (s, 3H, CH$_3$).

EXAMPLE 3

(E)-3-(2,2':5',2"-terthien-5-yl)propenoic Acid

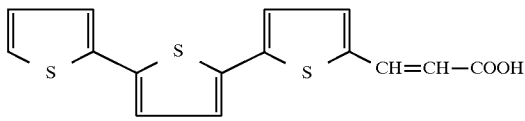

50 mg of the ester obtained from the example 2 are suspended in 3 ml of methanol. 0.5 ml of a 20% KOH solution are added to the suspension and the reaction mixture is refluxed for 56 h. At the end of the reaction the solvent is dry evaporated, the solid is treated with 6N HCl and extracted with chloroform.

The washed, dehydrated and evaporated extracts give a yellow solid; m.p.: 300° C. (dec.). NMR (DMSO, 200 MHz): 7.57–7.09 (m, 7H, α-T); 12.4 (s, b, 1H, COOH); 7.71 (d, 1H, =CH—COOH); 6.15 (d, 1H, α-T—CH=).

EXAMPLE 4

(E)-3-(2,2':5',2"-terthien-5-yl)propenoic acid N-hydroxy Succinimido Ester

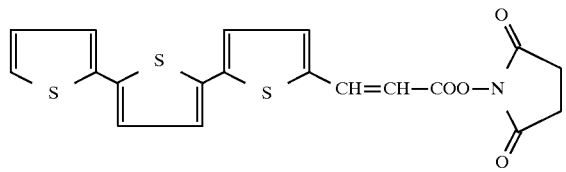

0.063 mmol of the acid obtained in the example 3 are suspended in 2 ml of DMF. 1.5 equivalents of N-hydroxysuccinimide are subsequently added to the suspension, the reaction mixture is stirred at room temperature and 0.063 mmol of dicyclohexylcarbodiimide solubilized in 5 ml of distilled dichloromethane were added.

The mixture is stirred at room temperature for 48 h. The solid obtained, constituted for the major part of dicyclohexylurea, is filtered out and washed with a little dichloromethane. The solutions are pooled, dry evaporated in order to remove the DMF, then the solid is treated with dichloromethane. The residual dicyclohexylurea, which is separated again, is removed and the solution evaporated after being water washed and dehydrated. A yellow solid is obtained.

NMR (CDCl$_3$, 200 MHz): 7.24–7.01 (m, 7H, α-T); 7.73 (d, 1H, =CH—COOCH$_3$); 6.18 (d, 1H, α-T -CH=); 2.84 (s, 4H, succinimide).

EXAMPLE 5

N-5-methyl-(2,2':5',2"-terthien-5-yl)-1-proline

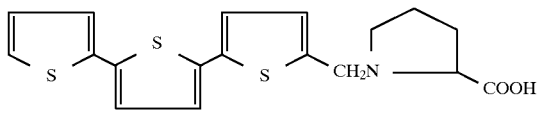

0.58 mmol of aldehyde described in the example 1 are suspended in 30 ml of methanol at room temperature and 1.15 mmol of proline and 300 mg of molecular sieves are added to the suspension.

After having saturated the reaction mixture with nitrogen, 100 mg of sodium cyanoborohydride are added and the mixture stirred for 12 h at room temperature. At the end of the reaction the solvent is dry evaporated and the greyish residue, after being treated with water and upon the elimination of the molecular sieves, is filtered.

A light yellow solid is obtained; m.p.: 157°–163° C. (dec.) (MeOH-DMF) darkening after light exposure.

Analysis: $C_{18}H_{17}NO_2S_3 \cdot \frac{1}{2}H_2O$ PM 384.5 Calculated: C: 56.63 H: 5.02 N: 5.09 Found: C: 56.88 H: 4.74 N: 5.10

NMR (DMSO, 200 MHz): 7.52–6.96 (m, 7H, α-T); 4.04 (AB sys, 2H, $CH_2$—N); 3.51–3.37 (m, 2H, Pro); 3.15–3.00 (m, 1H, Pro); 2.7–2.52 (m, 1H, Pro); 2.21–2.0 (m, 1H, Pro); 2.0–1.55 (m, 2H, Pro).

EXAMPLE 6

N-5-methyl-(2,2':5',2"-terthien-5-yl)-1-proline-N-hydroxy Succinimido Ester [α-TPOSu]

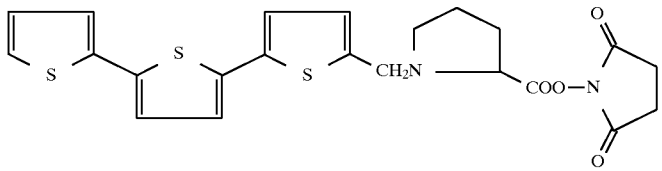

0.13 mmol of hydroxysuccinimido are added, at once, to 0.13 mmol of the compound obtained in the previous example, suspended in a solution of DMF 3 ml and dichloromethane 5 ml. The suspension is sonicated to allow for maximum solubilization of the reactants and added, at room temperature, with 0.13 mmol of dicyclohexyl-carbodiimide previously solubilized in 5 ml of dichloromethane.

The reaction mixture is stirred for 20 h at room temperature. The obtained solid is removed by filtration and the dry evaporated residual solution yielded a light yellow oil which solidified by adding petroleum ether to give the wanted product.

NMR (CDCl$_3$, 200 MHz): 7.26–6.87 (m, 7H, α-T); 4.10 (AB sys, 2H, CH$_2$—N); 3.78 (dd, 1H, H-CO-Pro); 3.10 (m, 1H, Pro); 2.82 (m, 1H, Pro); 2.84 (s, 4H, succinimide); 2.39–1.80 (m, 4H, Pro).

In the same way the N-5-methyl-(2,2':5',2"-terthien-5-yl)-1-proline-N-hydroxysulphosuccinimido ester was prepared.

EXAMPLE 7

N-methyl-N-5-methyl-(2,2':5',2"-terthien-5-yl) glycine

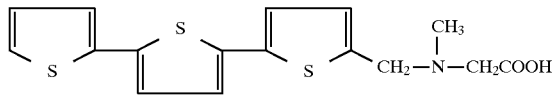

0.89 mmol of the aldehyde according to the example 1 are suspended in 50 ml of a methanol/acetic acid 99:1 mixture, previously deaerated and saturated with nitrogen. 3 equivalents of sarcosine and 0.5 equivalents of sodium cyanoborohydride are added at room temperature under stirring. The stirred reaction is sheltered from light for 24 h; during this time an abundant yellow precipitate is formed.

The solid so obtained, after being separated by filtration, is dried and crystallized from isopropyl alcohol/DMF; m.p.:230° C. (dec.).

Elementary Analysis: $C_{16}H_{15}NO_2S_3$ PM=349.47 Calculated: C: 54.98 H: 4.32 N: 4.00 Found: C: 55.02 H: 4.27 N: 4.31

Proceeding according to example 6 the following compounds were also obtained:

N-methyl-N-5-methyl-(2,2':5',2"-terthien-5-yl)glycine-N-hydroxy-succinimido ester N-methyl-N-5-methyl-(2,2':5',2"-terthien-5-yl)glycine-N-hydroxy-sulfosuccinimido ester N-methyl-N-5-methyl-(2,2':5',2"-terthien-5-yl)monomethyl succinimidate amide hydrochloride N-methyl-N-5-methyl-(2,2':5',2"-terthien-5-yl)-3-p-azido-phenyl-propanamide N-methyl-N-5-methyl-(2,2':5',2"-terthien-5-yl)-3-(2'-nitro-5'-azido)phenyl propanamide.

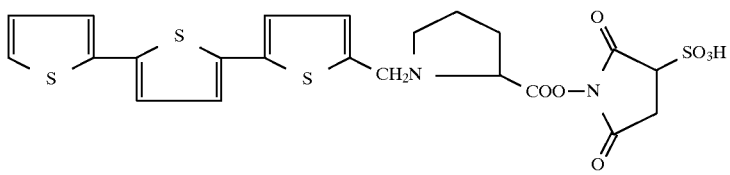 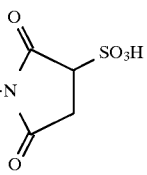

DERIVATIVES OF THE α-T REACTIVE TO THIOL GROUPS AND RELATED INTERMEDIATES

EXAMPLE 8

5-methylaminomethyl-2,2':5',2"-terthiophene

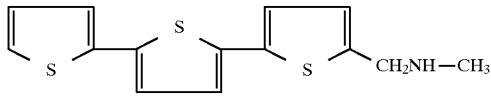

1.44 mmol of the aldehyde described in example 1 are suspended in 50 ml of degassed methanol and added with 6 equivalents of methylamine hydrochloride.

0.5 equivalents of NABH$_3$CN are added to the suspension and the mixture stirred at room temperature under nitrogen.

The reaction mixture is stirred for further 2 h sheltered from light then, the resulting suspension is partially evaporated.

The product purified by thin-layer chromatography (silica gel, chloroform: ethanol 93:7) allows to obtain a light yellow solid.

NMR (CDCl$_3$, 200 MHz): 7.35–6.82 (m, 7H, α-T); 3.93 (s, 2H, α-T-CH$_2$—); 2.51 (s, 3H, N—CH$_3$).

EXAMPLE 9

N-methyl-N-5-methyl-(2,2':5',2"-terthien-5-yl)-bromoacetamide [(α-T)-BrAc]

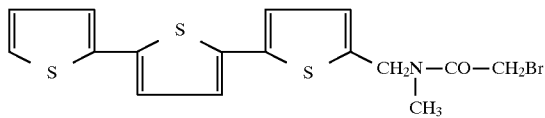

0.24 mmol of the amine obtained in the example 5 are solubilized in 50 ml of deaerated dichloromethane and kept under nitrogen.

To the solution cooled to 0° C. and sheltered from light 0.24 moles of N-hydroxysuccinimido ester of bromoacetic acid are added under stirring. After 30' the temperature is left rising to room values and kept at such values for 2 h.

The crystalline residue which results from solvent evaporation is treated with petroleum ether and purified by thin-layer chromatography (silica gel, chloroform). The light yellow crystalline solid obtained has m.p.:107°–109° C.

Analysis: C$_{16}$H$_{14}$BrNOS$_3$ PM=412.36 Calculated: C: 46.60 H: 3.44 N: 3.39 Found: C: 46.80 H: 3.37 N: 3.42

NMR (CDCl$_3$, 200 MHz): 7.23–6.88 (m, 7H, α-T); 4.72 and 4.68 (s, 2H, α-T-CH$_2$); 3.10 and 3.02 (s, 3H, N—CH$_3$); 3.95 and 3.89 (s, 2H, CO—CH$_2$—).

EXAMPLE 10

S,S-pyridyl-dithio-N-methyl-N-5-methyl-(2,2':5',2"-terthien-5-yl)propanamide

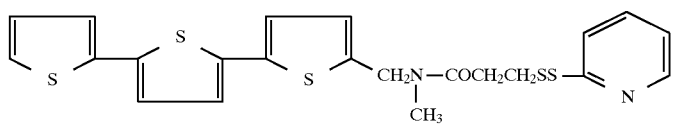

0.20 moles of the amine obtained in the example 5 are solubilized in 30 ml of distilled, degassed and saturated with nitrogen dichloromethane.

The solution is cooled to 0° C. and, sheltered from light and under stirring, added with 0.22 mmol of S,S-pyridyl-dithiopropionic-N-hydroxysuccinimido ester (SPDP) acid. After 1 h the solution is left rising to room temperature and stirred for further 48 h. The solvent is then fully evaporated and the residual product purified by column chromatography (silica gel, chloroform/methanol 98:2).

Analysis: C$_{22}$H$_{20}$N$_2$S$_5$O PM=488.7 Calculated: C: 54.06 H: 4.12 N: 5.73 Found: C: 53.57 H: 4.11 N: 5.72

NMR (CDCl$_3$, 200 MHz): 7.22–6.85 (m, 7H, α-T); 4.65 and 4.57 (s, 2H, CH$_2$—N); 2.93 and 3.00 (s, 3H, N—CH$_3$); 8.44 (ddd, 1H, Py); 7.75–7.58 (m, 3H, Py); 3.13 (t, 2H, CH$_2$); 2.78 (t, 2H, CH$_2$).

EXAMPLE 11

N-methyl-N-5-methyl-(2,2':5',2"-terthien-5-yl)-4-(N-maleimidomethyl)cyclohexyl-1-carboxyamide

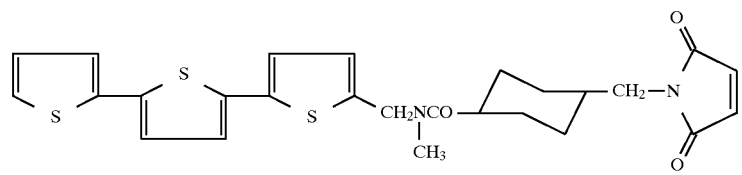

0.27 mmol of amine prepared according to the example 8 are solubilized in 2 ml of DMF.

The solution is diluted with 30 ml of dichloromethane nitrogen saturated and cooled to 0° C. 0.30 mmol (1.1 equivalents) of succinimidyl-4-(N-maleimidomethyl)-cyclohexano-1-carboxylate (SMCC) are added to the solution under stirring. Then the reaction mixture is warmed to 35° C. for 12 h and subsequently added with further 0.09 mmol of SMCC.

After 24 h of stirring the solvent is evaporated and the residual solid is purified by column chromatography (silica gel; $CHCl_3$) obtaining a crystalline solid.

α-T DERIVATIVES CONJUGABLE TO SACCHARIDIC RESIDUES

EXAMPLE 12

$N^\alpha$-methyl-$N^\alpha$-5-methyl-(2,2':5',2"-terthien-5-yl) glycyl Hydrazide

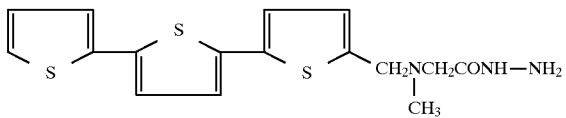

0.5 mmol of the product obtained as described in the example 7 (N-methyl-N-5-methyl-(2,2':5',2"-terthien-5-yl) glycine-N-hydroxysuccinimido ester) solubilized in 5 ml of anhydrous THF, are added drop by drop to 5 ml of a solution of hydrazine hydrate in 5% THF at 0° C., under vigorous stirring.

After 4 h the reaction mixture is evaporated and the oily residue purified by column chromatography (silica gel; $CHCl_3/CH_3OH$ 95:5) to give a light yellow solid; m.p. :158° C. NMR ($CDCl_3$, 200 MHz): 7.18–6.71 (m, 7H, α-T); 3.65 (s, 2H, $CH_2$); 2.27 (s, 3H, N—$CH_3$); 3.08 (s, 2H, N—$CH_2$—CO); 8.01 (s, br ex, 1H, NH); 3.75 (s, br ex, 2H, $NH_2$).

α-T DERIVATIVES CAPABLE OF REACTING WITH THYROSINE AND HYSTIDINE RESIDUES

EXAMPLE 13

N-methyl-N-5-methyl(2,2':5',2"-terthien-5-yl)-p-aminobenzamide

α-T DERIVATIVES LINKED TO BIOTIN

EXAMPLE 14

N,N'-dimethyl-N-5-methyl-(2,2':5',2"-terthien-5-yl)-N-biotinyl-1,2-diaminoethane 0.2 mmol of the aldehyde obtained in the example 1 are suspended in 30 ml of a $CH_3OH/CH_3COOH$ (99:1) mixture.

2 Equivalents of N,N'-dimethyl-N'-biotinyl-1,2-diaminoethane and 0.5 equivalents of sodium cyanoborohydride are added to the nitrogen satured suspension.

The suspension is stirred for 48 h then the solvent is evaporated, the residue is treated with water, filtered and purified by HPLC.

EXAMPLE 15

N-methyl-N-(2,2':5',2"-terthien-5-yl)-methyl-biotinamide 91 mg (0.44 mmoles) of dicyclohexylcarbodiimide are added to a suspension of 107 mg (0.44 mmoles) of Biotin and 55 mg (0.48 mmoles) of N-hydroxysuccinimide in DMF (1.5 ml).

The mixture is stirred at room temperature for 20 h and thereafter 140 mg (0.48 mmoles) of N-methyl-N-(2,2':5',2"-terthiophen-5-yl)methylamine solved in 10 ml DCM are added.

After 3 h at room temperature the formed dicyclohexylurea is filtered off and the organic phase is washed with $H_2O$ and dryed over $Na_2SO_4$. The solvent is eliminated by evaporation and the obtained solid is purified by HPLC ($H_2O$/TFA 0.1%—MeOH).

Functionalization of the Carrier

EXAMPLE 16

Conjugate (α-T)-concanavalin A

100 μl of a solution of αTPOSu 16.5 mg/ml are slowly added to 2 mg of concavalin A (produced by Sigma Company) (final conc. $3.5 \times 10^{-3}$ mmol) solubilized in 0.25 ml of 100 mM phosphate buffer (pH 8). The obtained suspension is gently stirred for a night at 4° C. in the dark.

After centrifugation, the surnatant, constitued of terthienylated Concanavalin A is purified by gel filtration on Sephadex G25 collecting the fractions showing a characteristic fluorescence.

The terthienylated concanavalin A has been characterized in terms of moles of α-T per mole of protein and this value turned out to be equal to 10.

EXAMPLE 17

Conjugate (α-T)-succinyl Concanavalin A (SuConA)

The terthienylation reaction of the SuConA has been worked out in a way analogous to what reported in the example 13.

The moles of α-T per mole of protein ratio turned out to be equal to 1.5, thus lower than the conjugate with concanavalin A owing to a lower availability of the amino groups.

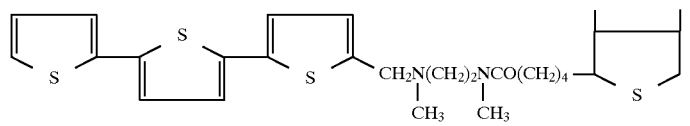 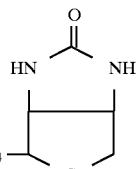

EXAMPLE 18

Conjugate (α-T)-Avidin

100 μl of solution 1.54 mg/ml in DMSO of αTPOSu (example 6) are added to 2 mg of avidine (Boheringer product) solubilized in 0.5 ml of 100 mmol phosphate buffer (pH 8). The suspension is gently stirred for one night at 4° C. in the dark, centrifuged, then the conjugate is purified by gel filtration on Sephadex G10® eluting with 100 MM phosphate buffer (pH 8), collecting the fluorescent fractions.

The ratio between the number of moles of α-terthienyl introduced per mole of Avidin has been obtained from the molar extinction coefficient value determined for the α-terthienyl derivative compared to the proteic one and turned out to be equal to 7.

EXAMPLE 19

Bovine Serum Albumin (BSA) has been dissolved in PBS at the concentration of 50 mg/ml; the aldehyde obtained according to the example 1 and the product obtained in the example 6 (αTPOSu) have been dissolved in dimethyl sulfoxyde (DMSO) at a concentration of 2 mg/ml.

In two parallel experiments 1.8 ml of BSA solution were allowed to react for one night at 4° C. in the dark with 0.2 ml of the two above mentioned solutions of the α-T derivatives. The day after a small aliquot of the two reaction products has been purified by gel filtration on PD-10 (Pharmacia) columns, in order to separate the terthienylated BSA from the terthienyl reactants if in excess. During the gel filtration it has been observed that the yellowish colouring of the α-T derivative quantitatively co-migrated with the proteic fraction, showing that the terthienyl compounds had reacted in quantitative manner with the protein. The raw reaction products and the products purified by gel filteration have finally been analysed by electrophoresis on acrylamide gel in native conditions, using fluorescein labelled BSA.

The bands in the gel have been visualized by irradiation with ultraviolet light and then the gel has been photographed in these conditions. Such analysis revealed that the terthienylation of the BSA with the two reactants gave a fluorescence well detectable by the two bands characteristic of the BSA on native gel, which migrated in a analogous way compared with the two bands of the fluorescein labelled BSA.

EXAMPLE 20

The monoclonal antibody 225–28S [Natali P. G. et al. J. Nat. Cancer Inst. 73, 13–24 (1984)] has been functionalized with αTPOSu at the amino-group residues using the following protocol.

50 μl of a solution of αTPOSu 14 mg/ml in DMSO (final conc. $1.3 \times 10^{-3}$ mmol, 200 equivalents) have been slowly added, by a variable volume pipet, to 1 mg of monoclonal 225-28S at a concentration of 5 mg/ml in 100 mM phosphate buffer, pH 8.

The so obtained milky suspension is gently stirred for 2 h at room temperature in the dark.

After this time the solid still present is removed by centrifugation and the solution of the labelled antibody is purified by gel filtration on Sephadex G25®).

The monoclonal labelling has been verified recording the UV spectrum of the pooled fractions obtained by the filtering purification, which shows two absorption maxima both at 280 nm and 360 nm and which are respectively due to the protein and to the presence of alfa terthienyl derivative.

From the measurement of the recorded UV absorptions (taking into account the value of $\epsilon^{360}=27000$ $LM^{-1}cm^{-1}$ for the alfa terthienyl derivative used) it is possible to estimate a labelling ratio of 3 moles of α-T per mole of protein.

EXAMPLE 21

A recombinant anti-lysozyme antibody, HyHEL-10 [Lavoie T. B. et al.: J. Immunol. 148, 503–513 (1992)], in scFv configuration [(G. Winter and C. Milstein: Nature, 349, 293 (1991); D. Neri, M. Momo, T. Prospero, G. Winter (1995) High affinity antigen binding by chelating recombinant antibodies (CRABS)—J. Mol. Biol., 246, 367–377)] in which a cysteine residue has been cloned at the C-terminal end of the molecule as single site of thiol-specific functionalization (in the following denoted as antibody scFv-cys), has been derivatized with the bromo acetamide compound described in the example 9 in the following way.

The antibody scFv-cys at a concentration of 1 mg/ml in PBS has been reduced for 15 minutes by addition of dithiothreitol (DTT) at a final concentration of 0.1 mM.

0.1 ml of a solution of bromo acetamide prepared according to the example 9 in DMSO (2 mg/ml; final concentration 0.48 mM) have been added to 0.9 ml of the reduced antibody solution, in order to have enough terthyenil derivative for both saturating the DTT present in solution and functionalizing the cysteines of the molecules of scFv-Cys. The reaction has been carried out for 2 h in ice, then stopped by addition of 0.1 ml of 100 mM DTT.

The terthienylated antibody has been purified by gel filtration on PD-10 (Pharmacia) column and the occurred terthienylation has been checked out by running a gel electrophoresis on acrylamide in denaturing conditions. The gel irradiated with ultraviolet light showed the presence of a fluorescent band of molecular weight of about 30000 dalton.

In the same way were prepared:

Mouse anti Herpes simplex Virus 1 and 2 antibody α terthienyl conjugate

Human anti Herpes simplex Virus 1 and 2 antibody Fab fragment-α-terthienyl conjugate Mouse anti Rubella virus α—terthienyl conjugate

BIOCIDAL EFFECT

EXAMPLE 22

Antibacteric Activity of Substituted Terthienyl Derivatives

The bacterial strain TG1 (*Escherichia coli*) containing a plasmid with the gene of resistance to ampicillin has been grown in medium 2xTY-100 μg/ml ampicillin till reaching a value of $A^{600}=0.5$.

Then the cells have been centrifuged, resuspended in PBS (10 times the original volume; $A^{600}=0.05$) in Petri dishes. To each dish a dilution 1:1000 of a stock solution of photosensitizer [PBS (negative control), α-T or (α-T)-CHO (according to the example 1)] in DMSO (1 mg/ml) has been added. The photosensitizer final concentration was therefore 1 μg/ml. The Petri dishes have been irradiated with gentle stirring by a UVP BLB lamp and plated in serial dilutions (10 μl and 100 μl) on plates of agar+2xTY+100 μg/ml ampicillin.

The bacteria photo-killing efficacy, not only by the α-T but also by the (α-T)-CHO derivative is easily detectable according to the number of colonies formed on plate after irradiation as shown in following Table I

TABLE I

|  | Colonies number | |
| --- | --- | --- |
|  | 10 µl | 100 µl |
| Negative control | $10^5$ | $10^6$ |
| (α-T)-CHO | 50 | 500 |
| α-T | 6 | 48 |

As shown the formil substituted terthienyl derivative keeps its biocidal activity.

EXAMPLE 23

Antitumoral Activity of Terthienylated Antibodies

The cellular line COLO-38, derived from a Human melanoma, and the monoclonal 225-28S terthienylated antibody according to example 18 [and in the following denoted as IgG-(α-T)] are used.

The α-T molecule/IgG molecule ratio has been estimated to be 1.6 on the basis of the conjugate absorption at 360 nm, using the absorption coefficient $\epsilon^{360}=27000$ LM$^{-1}$ cm$^{-1}$ for α-T, assuming quantitative recover of the protein used in the terthienylation, or from the molar extinction coefficients values $E^{360}=27000$ LM$^{-1}$ cm$^{-1}$ and $\epsilon^{280}=2700$ LM$^{-1}$ cm$^{-1}$ as a contribution of the absorption at 280 nm typical of the protein under examination.

COLO-38 cells, grown in RPMI medium added with 10% FETAL CALF SERUM (FCS), have been washed and parallely incubated in Petri dishes with IgG(α-T) (5 µM), IgG alone (5 µM), IgG-(α-T) not correlated (5 µM) or only with the medium in the negative controls.

The dishes have been irradiated at 350 nm for 30 minutes, then washed and left to incubate for 24 h in RPMI added with 10% FCS.

The dead and living cells percentage has been finally determined in the following way.

The cells have been incubated with propidium bromide and fluorescein diacetate, then washed and analysed with a confocal BioRad MRC 600® microscope. The propidium bromide intensely colours the dead cells DNA in red, while the fluorescein diacetate is efficiently hydrolized to a green fluorescent product by esterases present in living cells.

In this way the analysis by two wavelengths laser confocal microscopy leads to the number of dead and living cells within the population.

|  | % Killing | |
| --- | --- | --- |
|  | COLO 38 | HT 29 |
| IgG-(α-T) | >90 | 12 |
| IgG | 8 | 14 |
| PBS | 6 | 10 |

The results above related clearly show that the melanoma cells are efficiently killed by IgG(α-T) but neither by not labelled IgG nor in the negative control made with HT 29 cells. In particular comparing the "% killing" caused by IgG-(α-T) over HT 29 cells it is clear that the α-T localization, due to carrier molecule conjugate specific targeting, has as consequence the selective killing of the targeted cells.

EXAMPLE 24

A monoclonal antibody anti *Candida albicans* is functionalized with αTPOSu prepared as described in Example 6 at its amino residues according to the following procedure: 200 equivalents of αTPOSu solubilized in 100 µl of N-methyl-pyrrolidone where added to 0.32 mg of antibody in 100 µM Phosphate pH=8.5. The resulting solution was incubated 2 h at 37° C. then the resulting labelled antibody was purified by gel-filtration on Sephadex G25®.

The presence of α-T bounded to the protein was confirmed from the UV-spectrum of the fractions eluted from the column at the highest absorbing values at 280 nm and 360 nm (which refer respectively to the protein and the α-terthienyl derivative). The protein recover is practically 100% and the labelling ratio is about 5 moles of α-T for each mole of protein.

EXAMPLE 25

Antifungine Activity of Vehiculated α-T

A: Photokilling of *Candida albicans* (C.a.) and *Saccaromices cerevisiae* (S.c.) cells mediated by lectines labelled with α-T.

Following the previously described procedures (see examples 16 and 17) the product obtained in the example 6 (αPTOSu) has been conjugated to concanavalin A (ConA) and to succinyl-concanavalin A (SuConA), a concanavalin derivative able to bind a great variety of fungi, but very less susceptible of agglutination with respect to concanavalin A.

*Saccharomyces cerevisiae* and *Candida albicans* cultures, grown in Sabourad Dextrose broth at 37° C. for 4 h, were diluted up to a concentration of about $2.5 \times 10^4$ cells/ml.

Aliquots of 0.1 ml of these suspensions have been added in the sterile micro-plates wells by multi-channel pipet. Then 0.1 ml of solution having suitable concentration containing the terthienylated derivative to test have been added in the various wells.

The tested compounds were the α-T, ConA-(α-T), SuConA-(α-T), ConA, SuConA, IgG-(α-T) antimelanoma (see the example 23) at the α-terthienyl final concentration equal to $3 \times 10^{-6}$ M/l.

Samples of *Candida albicans* and *Saccaromices cerevisiae* suspensions containing no terthienyl-derivative acted as reference in the experiment. Suspensions of *Candida albicans* and *Saccaromices cerevisiae* thus prepared have been incubated in the dark for 0.5 h, then irradiated at 350 nm for 30 minutes. Aliquots of *Candida albicans* and *Saccaromices cerevisiae* treated as above said and, respectively, non-treated were deposited on Petri plates containing Sabouraud Dextrose Agar. The plates were incubated in the dark for 24 h at 33° and the growth of the treated and non-treated samples was evaluated.

| Compound | Final conc. α-T (M/l) | Final. Conc. ConA/SuConA (M/l) | % Growth of col. C.a. and S.c. (non-treat. = 100) | |
| --- | --- | --- | --- | --- |
| ConA-α-T | $3 \times 10^{-7}$ | $3 \times 10^{-8}$ | 0 | 0 |
| SuConA-αT | $5 \times 10^{-7}$ |  | 10 | 5 |
| α-T | $4 \times 10^{-6}$ |  | 90 | 100 |
| ConA |  | $3.4 \times 10^{-5}$ | 100 | 100 |
| SuConA |  | $1.4 \times 10^{-5}$ | 100 | 100 |
| IgG anti melan. α-T | $6.5 \times 10^{-6}$ |  | 80** |  |

**The colonies number increases up to 100 by washing the cells with a physiologic solution containing 0.01% Tween 20.

These results show that non-labelled lectines have no toxicity and non-vehiculated α-T can not bind to the cells and are not able to exert the cytotoxic action.

On the other hand lectines labelled with α-T bind specifically and are stable to washing showing a good photosensibilization after irradiation. Finally non-related proteins labelled with α-T, (IgGantimelanoma-α-T) which can not bind on the cells, show no photosensibilization capacity.

B: Photokilling mediated by specific α-T labelled anti *Candida albicans* antibodies.

The specific photosensibilization was evaluated on *Candida albicans* cell. A monoclonal antibody anti *Candida albicans* (C.a.) was labelled with α-TOSu according to the previously described procedure.

The terthienylated antibody, named IgG anti C.a.-α-T, containing 5 moles of α-T per mole of IgG, was used for the test of specific killing of this mycete.

To a suspension of *Candida albicans* cells, (ATCC 10231 in PBS pH 7.4, 0.5 McFarland), aliquots of α-T (final conc $4 \times 10^{-6}$ M/l), IgG anti C.a.-α-T (final conc. $6.5 \times 10^{-7}$ M/l of α-T), IgG anti HSV-α-T (final conc. $6.5 \times 10^{-6}$ M/l of α-T) and IgG anti C.a. non-terthienylated (same conc. as in the conjugates rapresenting the control), were added. The cells were incubated in the dark for 30', the supernatants eliminated and the cells washed three times with a physiologic solution and finally collected by centrifugation in order to eliminate the α-T or the terthienylated-antibody excess.

The cells suspension in PBS was irradiated with a 360 nm light for 30' and 20 μl aliquots deposited on Sabouraud-Agar plates which were incubated in the dark for 24 h at 33° C. The number of developed colonies was compared to the control (PBS).

|  | Final Conc. (M/l) | % colonies growth (control = 100) |
|---|---|---|
| IgGanti C.a.-α-T | $6.5 \times 10^{-7}$ | 0 |
| IgGanti HSV-α-T | $6.5 \times 10^{-6}$ | 85 |
| α-T | $4 \times 10^{-6}$ | 90 |
| IgGanti C.a. |  | 100 |
| PBS | 0 | 100 |

The above reported results show that only the terthienylated specific antibody binds to the cell wall of C.a cells producing a photodynamic effect "in situ" after irradiation at 360 nm.

EXAMPLE 26

The cutaneous phototoxicity of the α-terthienylated derivatives was tested by treatment of the depilated skin of albino guinea pigs.

The test was performed on male guinea pigs (weight 200–250 g) caged under controlled ventilation and at the temperature of 22° C.

On the abdomen skin of the animals, which was accurately depilated 24 hours before the test, 10 μl of a solution of proteic conjugates linked to α-T (for example ConA-α-T, see example 13, and IgG anti HSV1-α-T) were applied, maintaining similar concentration of α-T.

After 1 hour the skin was repeteadely washed (Tween 20 0.01% in PBS) and irradiated at 360 nm for 1 hour. The intensity of the erithemateous reaction was determined 48 hours after the irradiation.

The results show that the cutaneous phototoxicity of the conjugates depends on the carrier used. If the carrier binds aspecifically, as in the case of ConA, and therefore is not totally removed by washing, only a slight decrease of the toxicity is observed after washing with a detergent.

Conjugates prepared starting from antibodies which can recognise selectively the pathogenic-agent, which do not bind aspecifically on the skin, are completely removed by washing and do not show a toxic reaction, confirming their importance in the treatment of cutaneous infections.

| Conjugate (conc . . .) | Erythema intensity | |
|---|---|---|
|  | no washing | washing with detergent |
| ConA-α-T | 0.62 | 0.28 |
| IgG antiHSV1 | 0.03 | 0.0 |

Erythema intensity scale: 0 no erythema, 1 max. erythema)

The above reported examples clearly show that suitably vehiculated α-T, or its structural analogues, may be used for the selective and quantitative killing of biologically and clinically relevant targets such as cancer cells, bacteria and fungi.

Moreover the viruses killing mediated by vehiculated α-T, for example of the herpes virus, is particularly interesting due to the possibility to act on the infection at topical level either concerning the active principle application or for the irradiation modalities of the interested zone.

The terms "derivatized" and "functionalized" as used in the present application indicate, when referred to the terthienyl-moiety, the introduction in the molecule of groups capable of reacting with specific other groups while, when referred to a protein, indicate the introduction in the protein of the terthienyl-moiety.

We claim:

1. Conjugates comprising a carrier molecule and an organic molecule able to produce singlet oxygen after irradiation, wherein said organic molecule is a compound having formula (I) where $Z_1$, $Z_2$ and $Z_3$ are the same or different and are S or O, the organic molecule being suitably derivatized in order to react with an amino, thiol, saccharide, histidine or tyrosine group of the carrier molecule, and wherein the carrier molecule is selected from the group consisting of antibodies, peptides, haptamers, and sugars able to direct the organic molecule toward a biological target.

2. Conjugates as claimed in claim 1 wherein the compound having formula (I) is 2,2':5',2"-terthiophene derivatized to react with an amino, thiol or saccharide, hystidine, tyrosine groups of the carrier molecule, being bound to Biotin and to photoreactive side chains.

3. Conjugates as claimed in claim 1 wherein the carrier molecule is linked to the organic molecule by an avidin-biotin complex.

4. Conjugates as claimed in claim 1 in which the compound having formula (I) is derivatized in order to react with an amino group of the carrier molecule.

5. Compounds having formula (I) as claimed in claim 4 represented by the following formulas:

(E)-3-(2,2':5',2"-terthien-5-yl) propenoic N-hydroxy succinimido ester

N-(5-methyl-2,2':5',2"-terthien-5-yl)-1-proline-N-hydroxysuccinimido ester

N-methyl-N-(5-methyl-2,2':5',2"-terthien-5-yl)glycine-N-hydroxy-succinimido ester N-methyl-N-(5-methyl-2,2':5',2"-terthien-5-yl)glycine-N-hydroxy-sulfosuccinimido ester N-5-methyl-(2,2':5',2"-terthien-5-yl)-1-proline-N-hydroxy-sulphosuccinimido ester N-methyl-N-5-methyl-(2,2':5',2"-terthien-5-yl) monomethyl succinimidate amide hydrochloride N-methyl-N-5-methyl-(2,2':5',2''-terthien-5-yl)-3-p-azido-phenyl-propanamide N-methyl-N-5-methyl-(2,2':5',2''-terthien-5-yl)-3-(2'-nitro-5'-azido)phenyl propanamide.

6. Conjugates as claimed in claim 1 wherein the compound having formula (I) is derivatized in order to react with a thiol group of the carrier molecule.

7. Compounds having formula (I) as claimed in claim 6 represented by the following formulas:

N-methyl-N-(5-methyl-2,2':5',2''-terthien-5-yl)-bromo acetamide

S.S-pyridyl-dithio-N-methyl-(5-methyl-2,2':5',2''-terthien-5-yl)-propanamide

N-methyl-N-5-methyl-(2,2':5',2''-terthien-5-yl)-4-(N-maleimidomethyl)cyclohexyl-1-carboxyamide.

8. Conjugates as claimed in claim 1 wherein the compound having formula (I) is derivatized in order to react with a saccharide group of the carrier molecule.

9. Compounds having formula (I) as claimed in claim 8 represented by:

N-$^\alpha$methyl-N$^\alpha$-5-methyl-(2,2':5',2''-terthien-5-yl)glycyl hydrazid.

10. Conjugates as claimed in claim 1 wherein the compound having formula (I) is derivatized in order to react with a hystidine or thyrosine group.

11. Compound having formula (I) as claimed in claim 10 represented by:

N-methyl-N-5-methyl(2,2':5',2''-terthien-5-yl)-p-aminobenzamide.

12. Conjugates as claimed in claim 1 wherein the compound having formula (I) is derivatived in order to react with Biotin.

13. Compound having formula (I) as claimed in claim 12 represented by;

N,N'-dimethyl-N-5-methyl-(2,2':5',2''-terthien-5-yl)-N-biotinyl-1,2-diaminoethane;

N-methyl-N-(2,2':5',2''-terthien-5-yl)-methyl-biotinamide.

14. Conjugates as claimed in claim 1 obtained by conjugating:

α-terthienyl-proline-N-hydroxysuccinido-ester and concanavalin A;

α-terthienyl-proline-N-hydroxysuccinido-ester and succinyl-concanavalin A;

α-terthienyl-proline-N-hydroxysuccinido-ester and avidin α-terthienyl-CHO and BSA α-terthienyl-BrAc and single chain Fv recombinant antibody fragment-cys;

α-terthienyl-proline-N-hydroxysuccinido-ester and monoclonal antibody anti *C. albicans;*

α-terthienyl-proline-N-hydroxysuccinido-ester and monoclonal antibody anti Herpes Simplex Virus 1 and 2;

α-terthienyl-proline-N-hydroxysuccinido-ester and human monoclonal antibody anti Herpes Simplex Virus 1 and 2 Fab fragment;

α-terthienyl-proline-N-hydroxysuccinido-ester and monoclonal antibody anti Rubella Virus 1 and 2.

15. Antibacterial, antiviral, antifungal, and antitumoral compositions containing a conjugate according to claim 1, in combination with a suitable pharmaceutically acceptable excipients.

16. Compositions as claims in claim 15, in the form for oral, intramuscular and topical administration.

* * * * *